(12) United States Patent
Segawa

(10) Patent No.: US 7,766,167 B2
(45) Date of Patent: Aug. 3, 2010

(54) CAPSULE ENDOSCOPE STORAGE CASE

(75) Inventor: Hidetake Segawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 467 days.

(21) Appl. No.: 11/631,246

(22) PCT Filed: Dec. 12, 2005

(86) PCT No.: PCT/JP2005/022791

§ 371 (c)(1),
(2), (4) Date: Feb. 26, 2007

(87) PCT Pub. No.: WO2006/073041

PCT Pub. Date: Jul. 13, 2006

(65) Prior Publication Data

US 2008/0039675 A1      Feb. 14, 2008

(30) Foreign Application Priority Data

Jan. 5, 2005    (JP) .............................. 2005-000933

(51) Int. Cl.
*A61B 19/02*    (2006.01)
(52) U.S. Cl. ................... 206/439; 206/363; 422/292
(58) Field of Classification Search ................ 206/363, 206/438, 439, 461–470, 484–484.2; 220/359.1–359.5; 422/28

See application file for complete search history.

(56) References Cited

U.S. PATENT DOCUMENTS

| 4,124,141 | A | * | 11/1978 | Armentrout et al. ......... 206/439 |
| 4,482,053 | A | * | 11/1984 | Alpern et al. ............... 206/439 |
| 4,697,703 | A |   | 10/1987 | Will |
| 5,082,112 | A | * | 1/1992  | Dunklee ..................... 206/363 |
| 5,144,942 | A | * | 9/1992  | Decarie et al. .............. 206/363 |
| 5,219,077 | A | * | 6/1993  | Transue ..................... 206/438 |
| 5,221,007 | A | * | 6/1993  | Foos ......................... 206/363 |
| 5,246,109 | A | * | 9/1993  | Markle et al. ............... 206/363 |
| 5,379,895 | A | * | 1/1995  | Foslien ...................... 206/363 |
| 7,291,308 | B2 | * | 11/2007 | Wu et al. .................... 422/292 |
| 2003/0168370 | A1 |   | 9/2003 | Merboth et al. |

FOREIGN PATENT DOCUMENTS

| CN | 86208639 U | 12/1987 |
| JP | 60-123372  | 7/1985  |
| JP | 5-212058   | 8/1993  |

(Continued)

OTHER PUBLICATIONS

Japanese Office Action dated Jun. 1, 2010 with English Translation.

*Primary Examiner*—Bryon P Gehman
(74) *Attorney, Agent, or Firm*—Scully, Scott, Murphy & Presser, P.C.

(57) ABSTRACT

When an inner cover portion is accommodated in a blister pack, a retention space area a for accommodating a capsule endoscope is formed between the bottom face of the inner cover portion and the inside bottom face of the blister pack. The capsule endoscope, retained by a retaining portion formed in the blister pack and by a hole portion formed in the inner cover portion, is set into a storage case. The entire capsule endoscope accommodated in the storage case is uniformly and satisfactorily sterilized by blocking the opening of the blister pack with a sterilizing sheet.

10 Claims, 12 Drawing Sheets

FOREIGN PATENT DOCUMENTS

| | | |
|---|---|---|
| JP | 7-187249 | 7/1995 |
| JP | 10-286263 | 10/1998 |
| JP | 11-193010 | 7/1999 |
| JP | 2000-60791 | 2/2000 |
| JP | 2000-185055 | 7/2000 |
| JP | 2002-17824 | 1/2002 |
| JP | 2002-34890 | 2/2002 |
| JP | 2003-523795 | 8/2003 |
| JP | 2004-261240 | 9/2004 |
| WO | WO 2001-35813 A1 | 5/2001 |

* cited by examiner

CAPSULE ENDOSCOPE STORAGE CASE

TECHNICAL FIELD

The present invention relates to a capsule endoscope storage case which accommodates an intra-subject information acquiring device such as a swallowable capsule endoscope which is introduced into a subject to acquire image information on an inside of the subject.

BACKGROUND ART

Recently, a capsule endoscope having an imaging function and a wireless communication function has appeared. During an observation period of time until the capsule endoscope is naturally discharged from a living body (human body) of a person to be examined after it is swallowed by a person to be examined as a subject for the purpose of observation (examination), the imaging function is sequentially performed with the movement of the capsule endoscope resulting from the peristalsis of the inside of organs (inside of the body cavity) such as stomach and small intestine.

During the observation period with the movement in the organs, image data picked up in the body cavity by the capsule endoscope are sequentially transmitted to an external device disposed outside the subject by means of the wireless communication function of radio communication and are stored in a memory disposed in the external device. By allowing the person to be examined to carry the external device having the wireless communication function and the memory function, the person to be examined can move freely during the observation period until the capsule endoscope is discharged after it is swallowed. After the observation, a doctor or a nurse can display the image of the body cavity on display unit such as a display to diagnose the health of the person to be examined on the basis of the image data stored in the memory of the external device.

An example of such a type of capsule endoscope includes a swallowable type shown in Patent Document 1, which discloses a configuration that a reed switch to be turned on or off by an external magnetic field is provided therein so as to control the driving of the capsule endoscope and the capsule endoscope is accommodated in a package including a permanent magnet for supplying the external magnetic field. That is, the reed switch disposed inside the capsule endoscope maintains its OFF state under an environment with a magnetic field greater than a predetermined intensity and is turned on with the decrease in intensity of the external magnetic field. For this reason, the capsule endoscope is not driven in the state where it is accommodated in the package. When the capsule endoscope is swallowed, the capsule endoscope is taken out of the package and the capsule endoscope is separated from the permanent magnet and thus is not affected by the magnetic force, thereby starting its operation. Due to such a configuration, the capsule endoscope can be suppressed from its operation in the state where it is accommodated in the package and can pick up an image using the imaging function and transmit image signals using the wireless communication function of the capsule endoscope after it is taken out of the package.

Patent Document 1: International Publication No. 01/35813 Pamphlet

DISCLOSURE OF THE INVENTION

Problem to be Solved by the Invention

The capsule endoscope needs to be sterilized before the capsule endoscope is used for the person to be examined. However, since the capsule endoscope is accommodated in the package in the state where it is retained, for example, by an O ring, it is difficult to allow the sterilizing gas to invade the package and to sterilize a contact surface between the O ring and the capsule endoscope or a contact surface between the package and the capsule endoscope, thereby not sterilizing the entire capsule endoscope uniformly.

In view of the foregoing, an object of the present invention is to provide a capsule endoscope storage case in which the entire capsule endoscope accommodated in the storage case can be uniformly and satisfactorily sterilized. Another object of the present invention is to provide a capsule endoscope storage case which can surely retain a capsule endoscope.

Means for Solving Problem

A capsule endoscope storage case according to one aspect of the present invention includes a first retainer and a second retainer that form a retention space area for retaining a capsule endoscope therebetween, and accommodate and retain the capsule endoscope in the retention space area; and a sterilizing sheet that blocks the retention space area, having a sterilizing gas permeability.

In the capsule endoscope storage case according to the present invention, one of the first and the second retainers may be accommodated in the other one of the first and the second retainers.

The capsule endoscope storage case according to the present invention may further include a passage that enables passing of the sterilizing gas between the first and the second retainers.

The capsule endoscope storage case according to the present invention may further include a hole portion that enables passing of the sterilizing gas in at least one of the first and second retainers.

In the capsule endoscope storage case according to the present invention, at least one of the first and second retainers may be formed in a mesh form which enables passing of the sterilizing gas.

In the capsule endoscope storage case according to the present invention, the first and the second retainers may retain the capsule endoscope accommodated in the retention space area in one of a point contact manner and a line contact manner.

In the capsule endoscope storage case according to the present invention, the accommodated capsule endoscope may be retained by at least one of the first and the second retainers, and accommodated in the retention space area.

EFFECT OF THE INVENTION

The capsule endoscope storage case according to the present invention can surely retain the capsule endoscope by accommodating the capsule endoscope in the retention space area formed between the first and second retainers, and can uniformly and satisfactorily sterilize the entire capsule endoscope accommodated in the storage case by providing the sterilizing sheet having a sterilizing gas permeability so as to block the retention space area.

EXPLANATIONS OF LETTERS OR NUMERALS

1 SUBJECT
2 CAPSULE ENDOSCOPE
3 RECEIVING DEVICE
4 DISPLAY DEVICE
5 PORTABLE RECORDING MEDIUM
11 AIRTIGHT CONTAINER
11a FRONT-HEAD COVER
11a1 MIRROR-FINISHED PORTION
11b BODY COVER
20 LIGHT EMITTING DEVICE (LED)
21 LED DRIVING CIRCUIT
22 SOLID-STATE IMAGING ELEMENT
23 CCD DRIVING CIRCUIT
24 RF TRANSMITTING UNIT
25 TRANSMITTING ANTENNA UNIT
26 SYSTEM CONTROL CIRCUIT
27 IMAGING LENS
29 BATTERY
31 RECEIVING JACKET
32 EXTERNAL DEVICE
40 STORAGE CASE
40a RETENTION SPACE AREA
40b PASSAGE
41 BLISTER PACK
41a, 42a CYLINDRICAL PORTION
41b, 42b HANDGRIP PORTION
41c, 42c EDGE PORTION
41d, 42d PROJECTION PORTION
41e, 42e BOTTOM FACE
41e1 OUTSIDE BOTTOM FACE
41e2 INSIDE BOTTOM FACE
41e3 RETAINING PORTION
41e4 PROJECTION PORTION
42 INNER COVER PORTION
42e1 HOLE PORTION
42e2 PROJECTION
42e3 STEP PORTION
42f, 42g HOLE PORTION
43 STERILIZING SHEET

BEST MODE FOR CARRYING OUT THE INVENTION

Hereinafter, exemplary embodiments of a capsule endoscope storage case according to the present invention will be described in detail with reference to FIGS. 1 to 16. The present invention is not limited to the exemplary embodiments, but may be modified in various forms without departing from the scope of the invention.

First Embodiment

Figure 1:
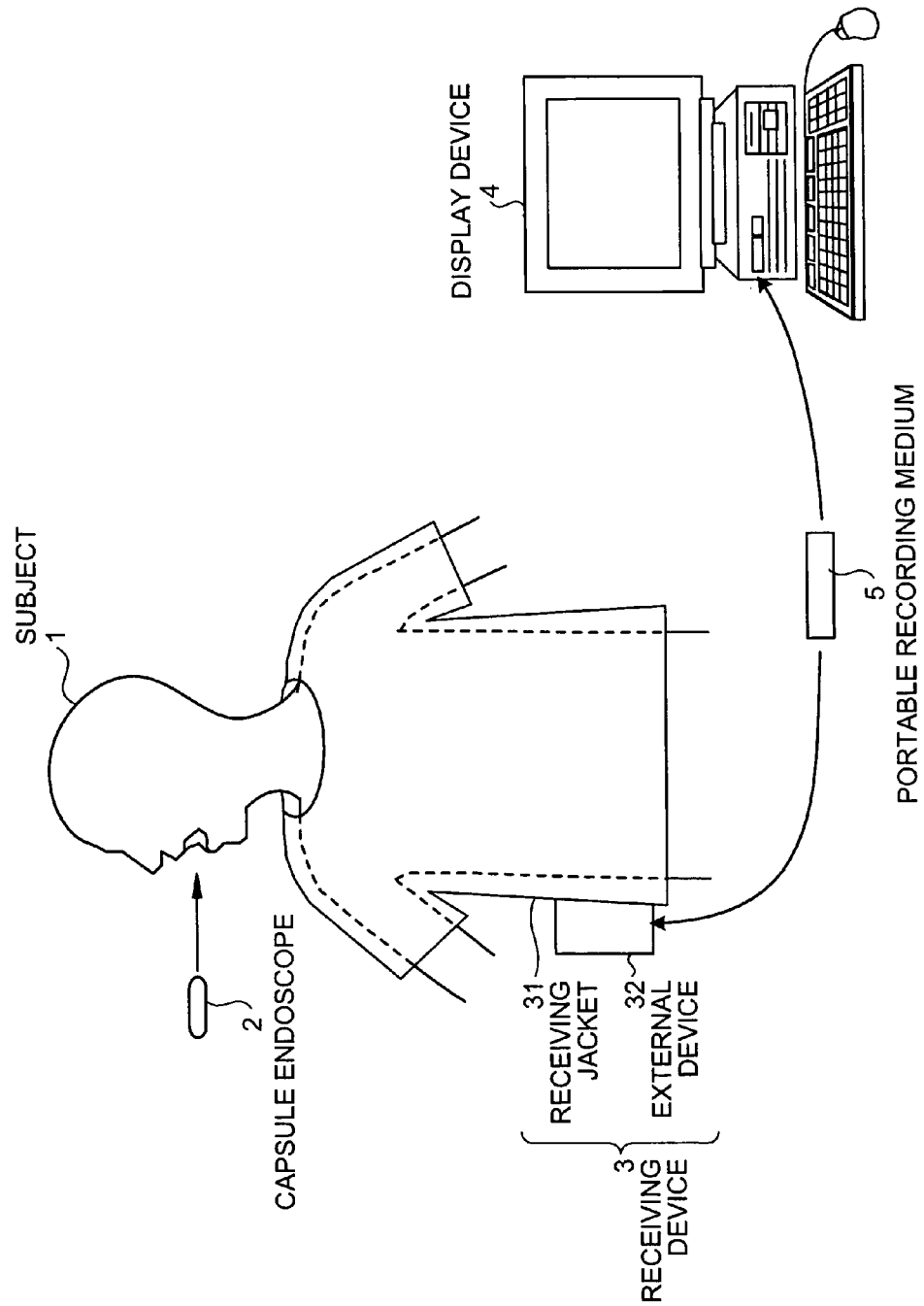
FIG. 1 is a conceptual diagram illustrating a concept of a wireless intra-subject information acquisition system according to the present invention.

FIG. 1 is a conceptual diagram illustrating a concept of a wireless intra-subject information acquisition system according to the present invention. In FIG. 1, a capsule endoscope system includes a swallow-type capsule endoscope 2 as a wireless intra-subject information acquisition device which is introduced into a body cavity of a subject 1 and a receiving device 3 as an external device which is disposed outside the subject 1 and which transmits and receives a variety of information with respect to the capsule endoscope 2 wirelessly. The wireless intra-subject information acquisition system includes a display device 4 displaying an image on the basis of data received by the receiving device 3 and a portable recording medium 5 for inputting and outputting data between the receiving device 3 and the display device 4.

As shown in the side sectional view of FIG. 2, the capsule endoscope 2 includes an airtight container 11 which is an outer case, a plurality of light-emitting elements 20 such as LEDs emitting illuminating light which is disposed inside the airtight container 11 so as to illuminate a subject portion in the body cavity, a solid-state imaging device 22 such as CCD and CMOS (hereinafter, referred to as "CCD 22") receiving reflected light of the illuminating light and imaging the subject portion, an imaging lens 27 forming an image of an object on the CCD 22, an RF transmitting unit 24 modulating image information acquired by the CCD 22 into RF signals and transmitting the RF signals, a transmitting antenna unit 25 emitting electromagnetic radiation of the RF signals, and a battery 29.

The airtight container 11 has a size which can be swallowed by a person and forms the outer case sealing liquid-tightly the inside thereof by elastically fitting a semi-spherical front-head cover 11a and a cylindrical body cover 11b to each other. The front-head cover 11a has a semi-spherical dome shape and the rear side of the dome is opened in a circular shape. The front-head cover 11a is formed of a transparent member having transparency or a light permeability, such as cycloolefin polymer or poly carbonate suitable for securing optical performance or strength, and has a mirror-finished portion 11a1 of which the surface has been subjected to a specular finish process, thereby transmitting the illuminating light from the light-emitting element 20 to the outside of the airtight container 11 and transmitting the reflected light from the subject due to the illuminating light to the inside thereof. The mirror-finished portion 11a1 is formed in a predetermined specular finish range (a range indicated by a dot-chained line a and a in FIG. 2) determined by an imaging range of the solid-state imaging device 11, etc.

The body cover 11b is a member which is disposed at the rear end of the front-head cover 11a so as to cover the elements. In the body cover 11b, a cylindrical body portion and a rear end portion of a semi-spherical dome shape are formed in a body and the front side of the body portion is opened in a circular shape. The body cover 11b is made of polysulfon suitable for securing strength. An illuminating unit, an imaging unit and a battery 29 to be described later are accommodated in the body portion and a wireless communication unit is accommodated in the rear end portion.

Figure 3:
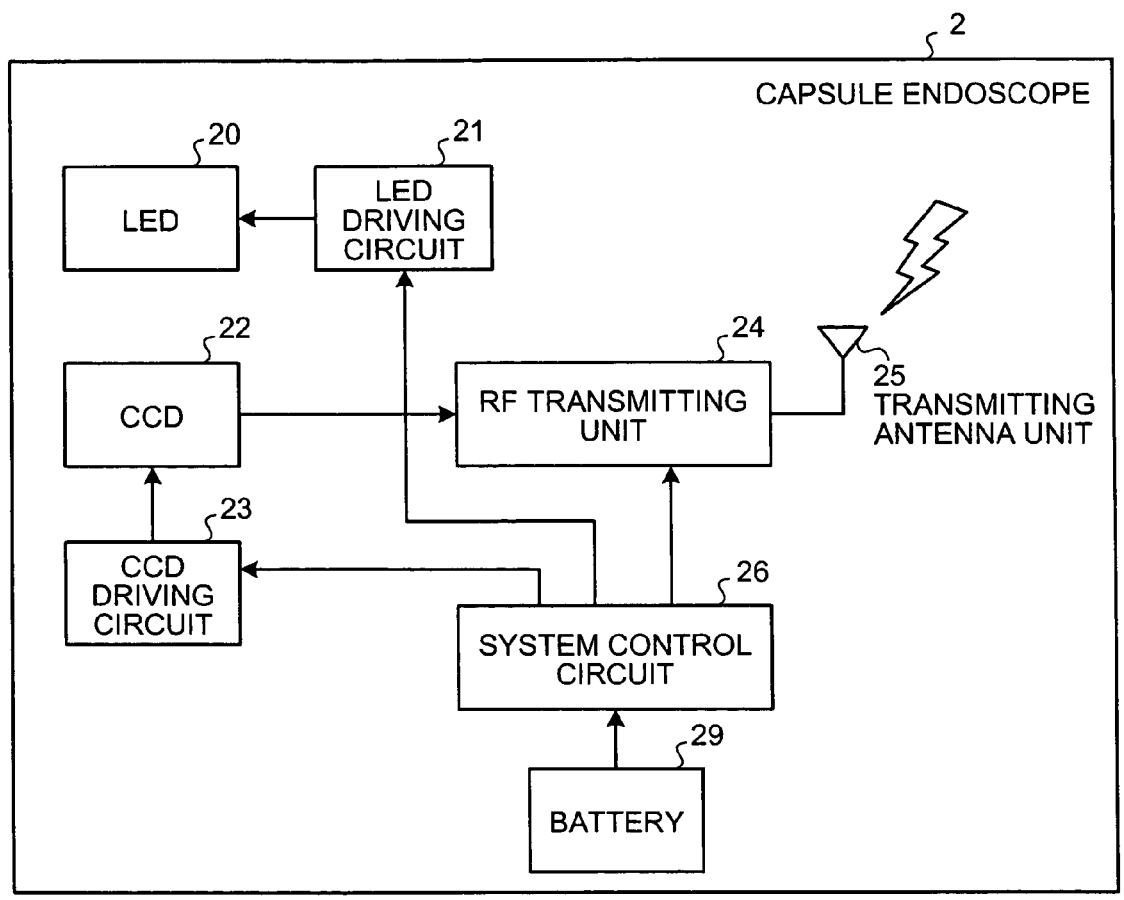
FIG. 3 is a block diagram illustrating an inner configuration of the capsule endoscope shown in FIG. 2.

As shown in the block diagram of FIG. 3, the capsule endoscope 2 includes an LED driving circuit 21 controlling driving states of an LED 20 and an LED 20 as the illuminating unit, a CCD driving circuit 23 controlling driving states of a CCD 22 and a CCD 22 as the imaging unit for capturing an image (intra-subject information) of the body cavity, which is reflected light from an area illuminated by the LED 20, by the use of the imaging lens 27, and an RF transmitting unit 24 and a transmitting antenna unit 25 as the wireless communication unit.

The capsule endoscope 2 has a system control circuit 26 controlling operations of the LED driving circuit 21, the CCD driving circuit 23, and the RF transmitting unit 24 and thus image data of a subject portion illuminated by the LED 20 are acquired by the CCD 22 while the capsule endoscope 2 is introduced into the subject 1. The acquired image data are converted into RF signals by the RF transmitting unit 24 and are transmitted to the outside of the subject 1 through the transmitting antenna unit 25. The capsule endoscope 2 has a battery 29 supplying power to the system control circuit 26 and the system control circuit 26 has a function of distributing the driving power supplied from the battery 29 to other elements (function executing unit).

The system control circuit 26 includes switch elements and latch circuits having switching functions, which are connected between the elements and the battery 29. When a magnetic field is applied from the outside, the latch circuit turns on the switch elements and then holds the ON state thereafter, thereby supplying the driving power from the battery 29 to the elements of the capsule endoscope 2. In this embodiment, the imaging unit having an imaging function, the illuminating unit having an illuminating function, and the wireless transmitting unit having a wireless function, which are all disposed inside the capsule endoscope 2, are collectively called function executing unit for executing predetermined functions. Specifically, the elements other than the system control circuit 26 are the function executing unit for executing predetermined functions.

As shown in FIG. 1, the receiving device 3 has a function as wireless receiving unit for receiving image data of the body cavity transmitted from the capsule endoscope 2 wirelessly. The receiving device 3 is worn by the subject 1 and includes a receiving jacket 31 having a plurality of reception antennas not shown and an external device 32 for processing the received RF signals.

The display device 4 serves to display the intra-body cavity image picked up by the capsule endoscope 2 and has a configuration such as a work station for displaying an image on the basis of data acquired from the portable recording medium 5. Specifically, the display device 4 may display directly an image by a CRT display, a liquid crystal display, and the like or may output the image to another medium, like a printer.

The portable recording medium 5 can be connected to the external device 32 and the display device 4 and has a structure capable of outputting or recording information when it is connected to both. In this embodiment, the portable recording medium 5 is inserted into the external device 32 and records the data transmitted from the capsule endoscope 2 while the capsule endoscope 2 is moving in the body cavity of the subject 1. Next, after the capsule endoscope 2 is discharged from the subject 1, that is, after the imaging operation of the subject 1 is finished, the portable recording medium is taken out from the external device 32 and is inserted into the display device 4, whereby the data recorded in the portable recording medium 5 are read out by the display device 4. For example, the portable recording medium 5 is composed of a Compact Flash (registered trademark) memory or the like and data can be indirectly input to and output from the external device 32 and the display device 4. Accordingly, unlike a case where the external device 32 and the display device 4 are directly connected to each other by wire, the subject 1 can freely move during the imaging of the body cavity.

Figure 8:
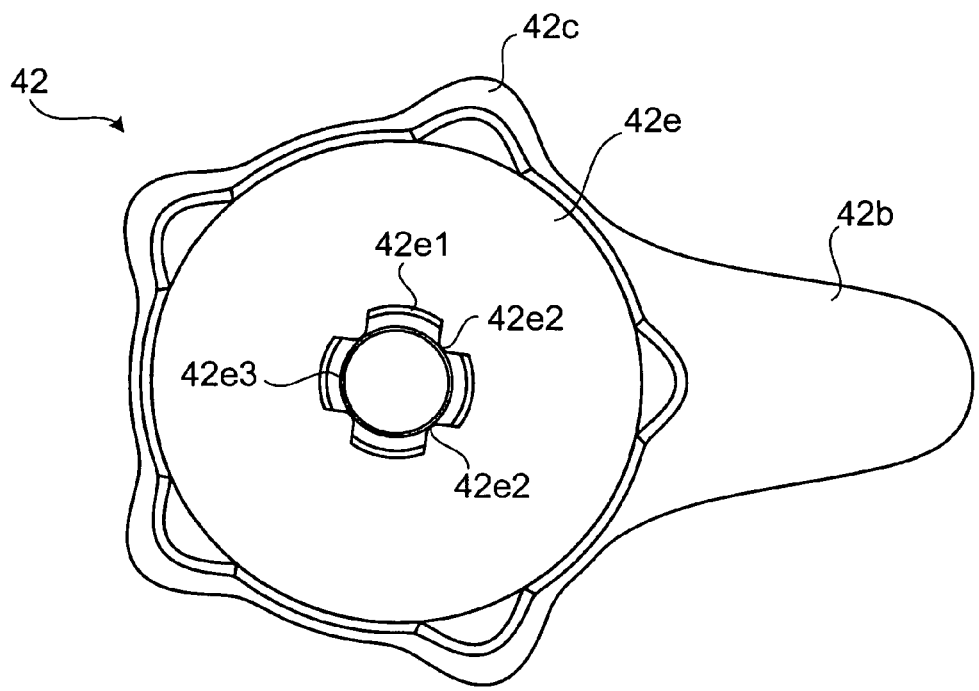
FIG. 8 is a top view illustrating a top surface of a inner cover portion according to a first embodiment shown in FIG. 5.
Figure 9:
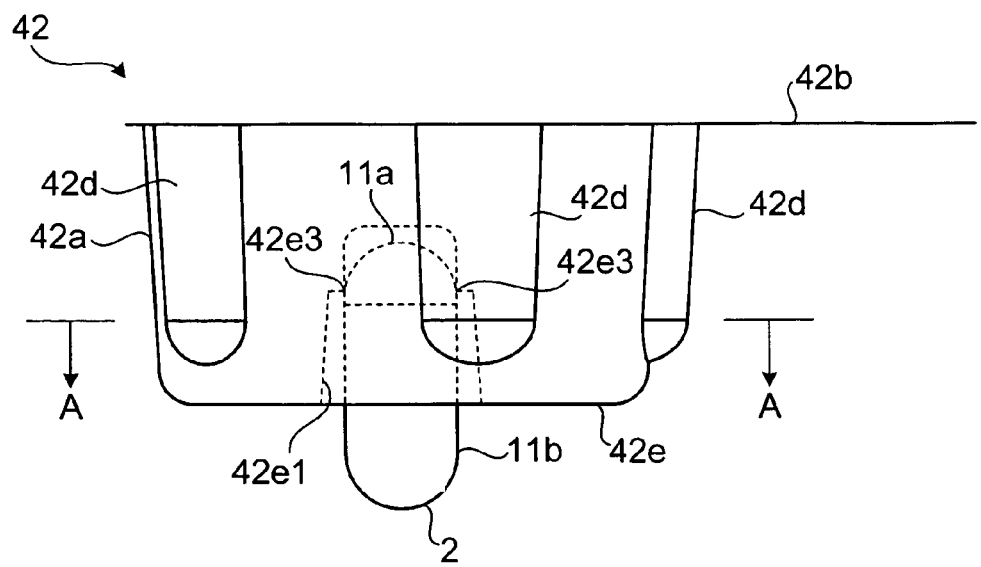
FIG. 9 is a side sectional view illustrating a side surface of the inner cover portion according to the first embodiment shown in FIG. 5.
Figure 10:
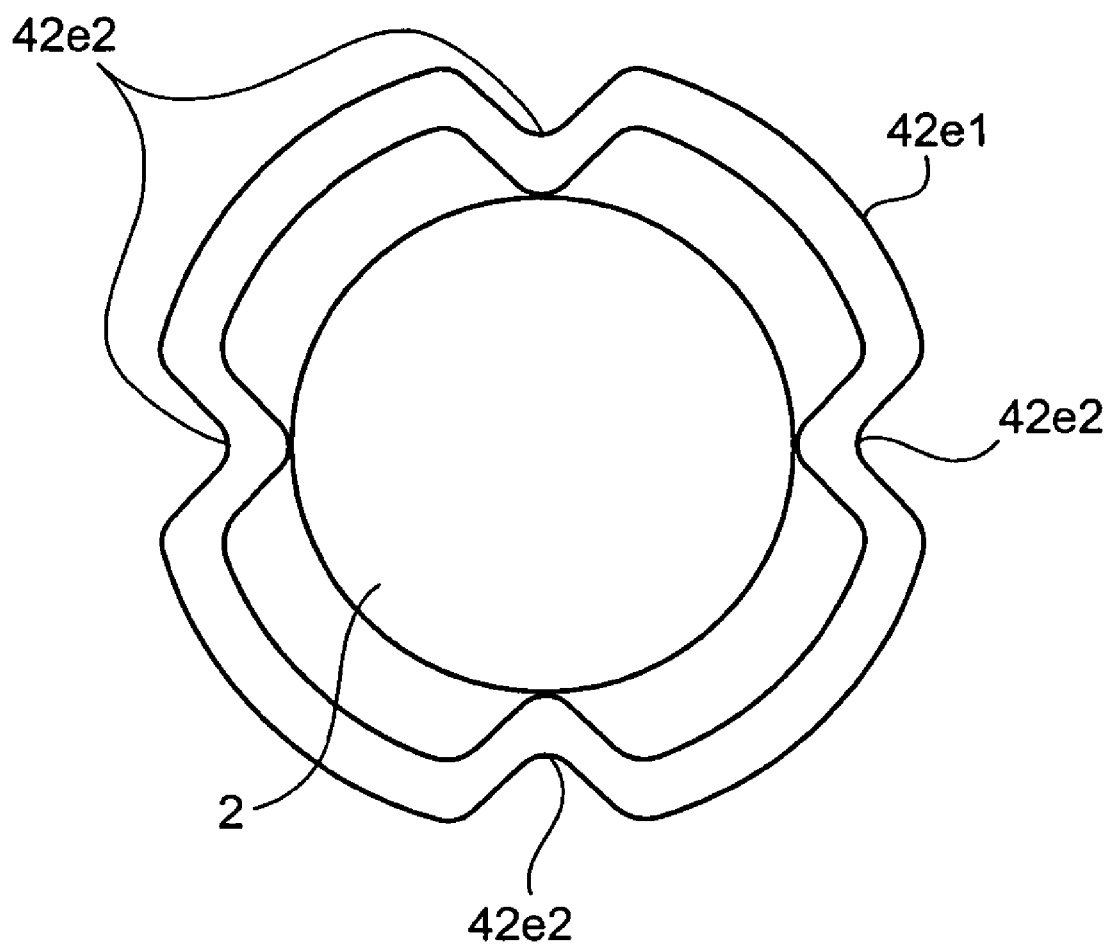
FIG. 10 is an enlarged sectional view of a hole portion taken along Line A-A of FIG. 9.
Figure 11:
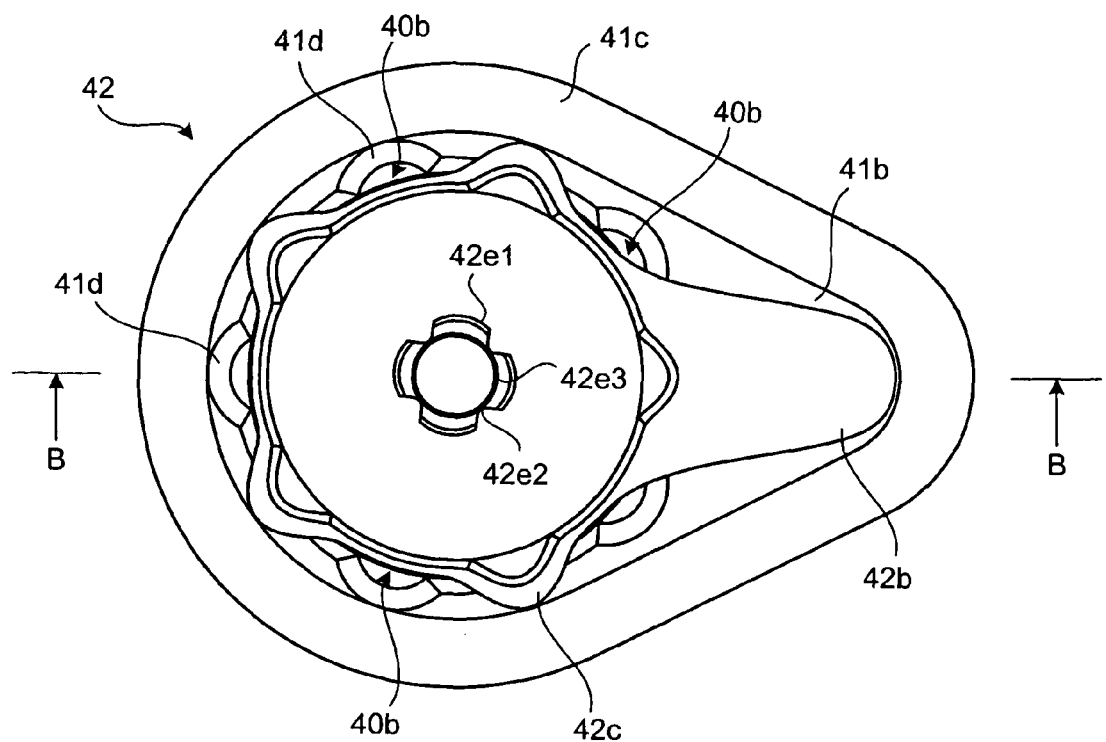
FIG. 11 is a top view illustrating a top view of the storage case shown in FIG. 5.
Figure 12:
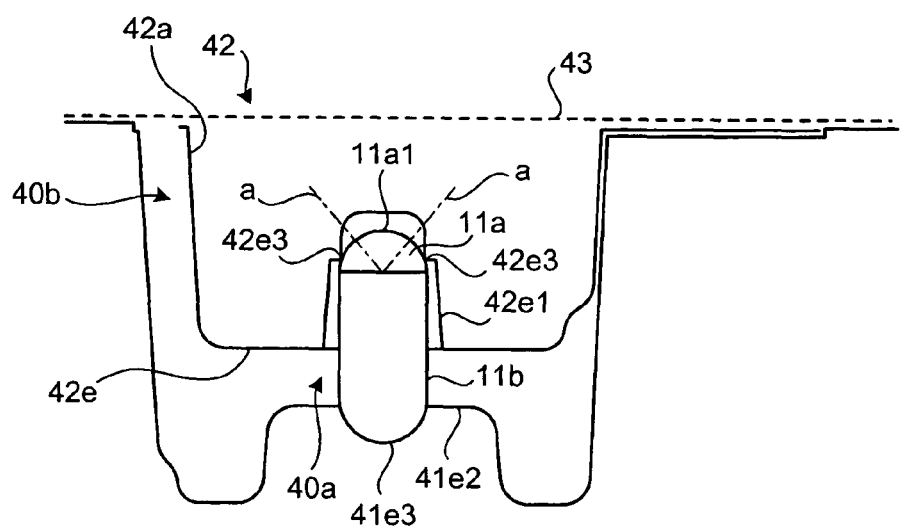
FIG. 12 is a cross-sectional view taken along Line B-B of FIG. 11.

The capsule endoscope having the function executing unit needs to be sterilized and be kept sterilized before it is used for a person to be examined. Accordingly, in this embodiment, the capsule endoscope 2 is accommodated in a storage case which can be sterilized. Hereinafter, the storage case according to a first embodiment is described with reference to FIGS. 4 to 12. Here, FIG. 4 is a perspective view illustrating a configuration of the storage case receiving the capsule endoscope, FIG. 5 is a perspective view illustrating an example where a sterilizing sheet is removed from the storage case shown in FIG. 4, FIG. 6 is a top view illustrating a top surface of the storage case shown in FIG. 5, FIG. 7 is a side sectional view illustrating a side surface of the storage case shown in FIG. 5, FIG. 8 is a top view illustrating a top surface of an inner cover portion according to a first embodiment, FIG. 9 is a side sectional view illustrating a side surface of the inner cover portion according to the first embodiment shown in FIG. 5, FIG. 10 is an enlarged sectional view of a hole portion taken along Line A-A of FIG. 9, FIG. 11 is a top view illustrating a top view of the storage case shown in FIG. 5, and FIG. 12 is a cross-sectional view taken along Line B-B of FIG. 11.

Figure 4:
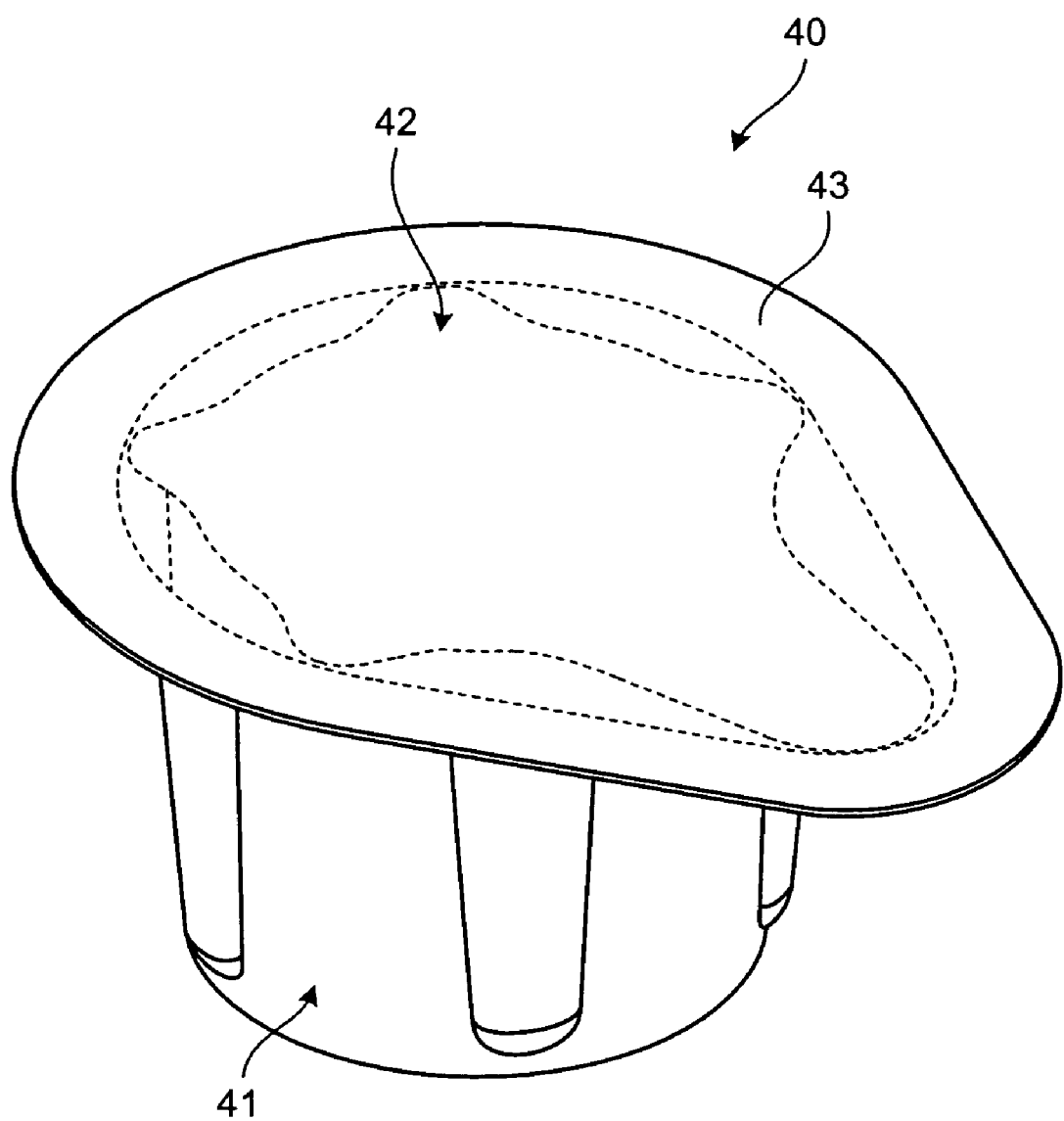
FIG. 4 is a perspective view illustrating a configuration of a storage case for receiving the capsule endoscope.
Figure 5:
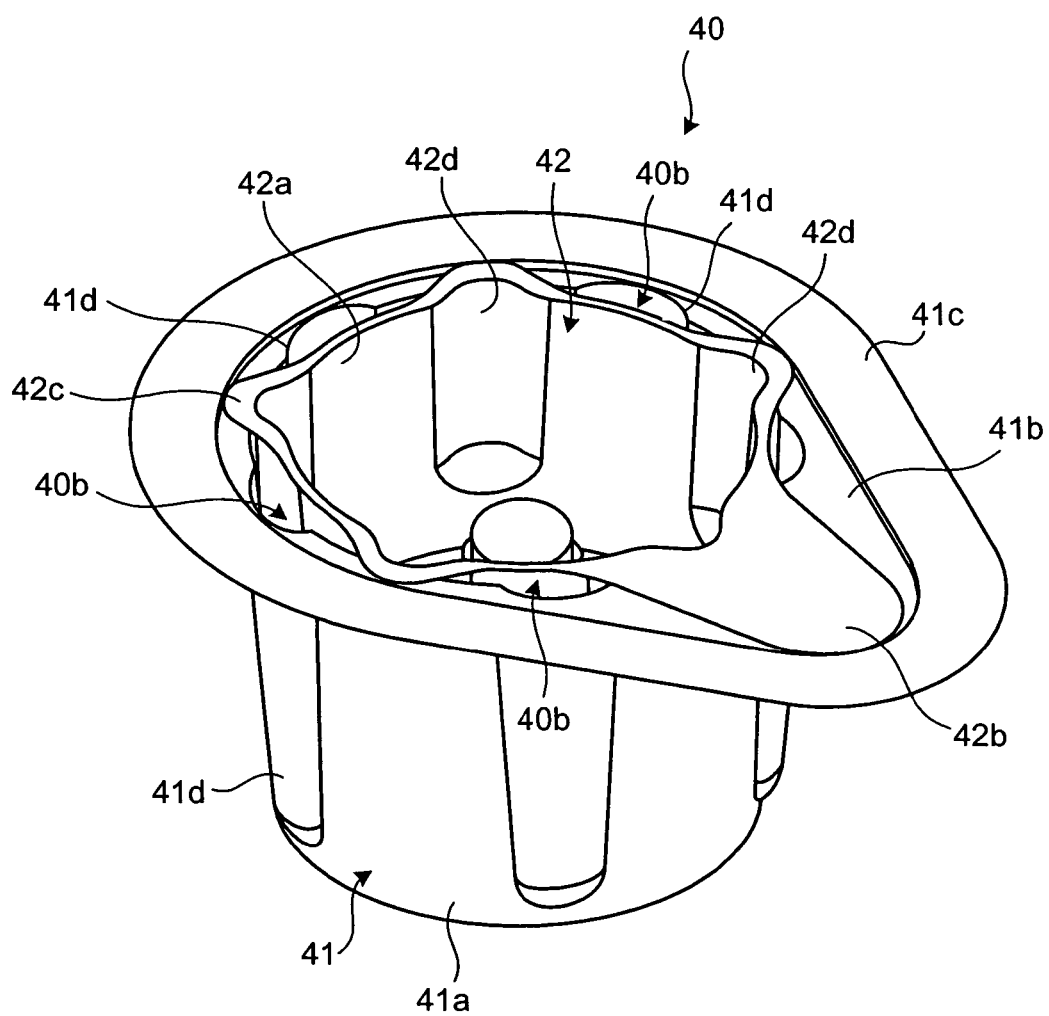
FIG. 5 is a perspective view illustrating an example where a sterilizing sheet is removed from the storage case shown in FIG. 4.

First, as shown in FIGS. 4 and 5, the storage case 40 includes a blister pack 41 having an outer receiving portion which can receive the capsule endoscope 2 therein, an inner cover portion 42 which is disposed in the blister pack 41 and has an inner receiving portion retaining the capsule endoscope 2 between the blister pack 41 and the inner cover portion, and a sterilizing sheet 43 which is disposed on the top surface of the blister pack 41 so as to block the opening of the blister pack 41. The blister pack 41 and the inner cover portion 42 constitute first and second retainers.

Figure 6:
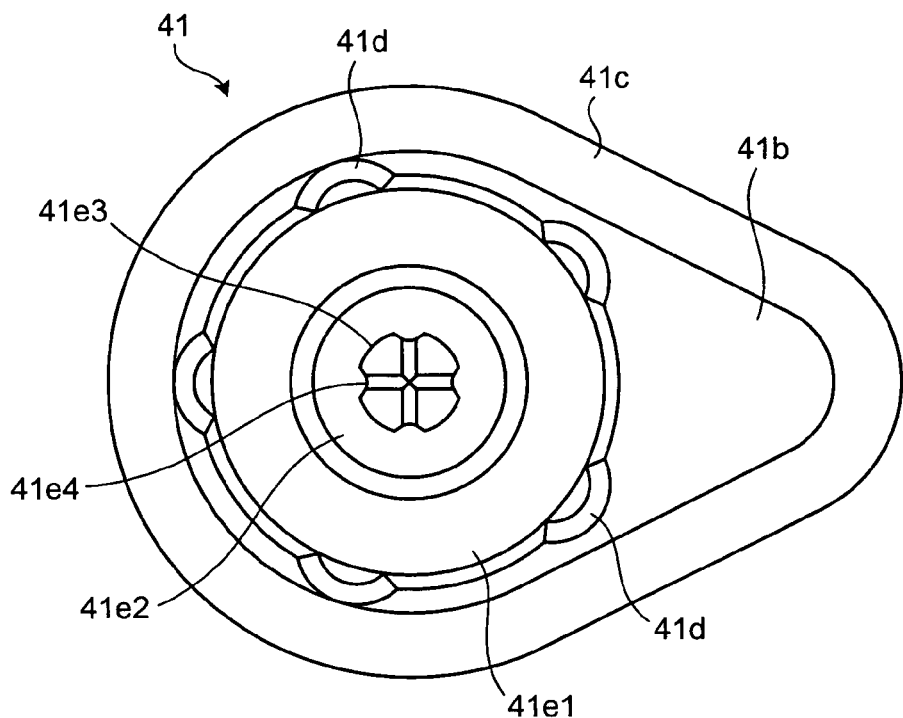
FIG. 6 is a top view illustrating a top surface of the storage case shown in FIG. 5.
Figure 7:
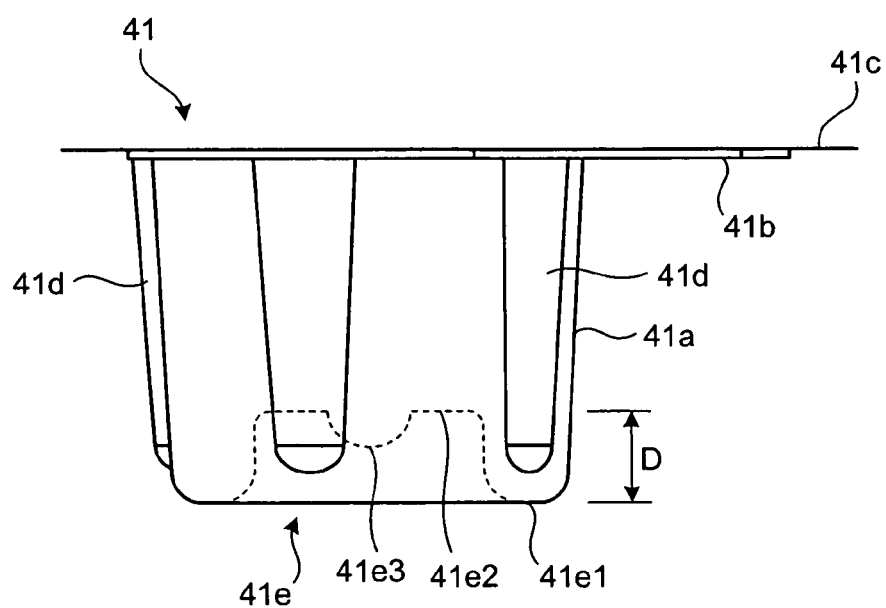
FIG. 7 is a side sectional view illustrating a side surface of the storage case.

As shown in FIGS. 6 and 7, the blister pack 41 includes a cylindrical portion 41a having a bottom, a tongue-shaped handgrip portion 41b disposed on a part of the upper edge of the opening of the cylindrical portion 41a, an edge portion 41c disposed on the upper edge of the opening of the cylindrical portion 41a and the outer circumference of the handgrip portion 41b, and a plurality of semi-cylindrical projection portions which is disposed on the circumferential surface of the cylindrical portion 41a so as to protrude from the inside of the cylindrical portion 41a to the outside.

The cylindrical portion 41a has a bottom face 41e and the bottom face 41e includes an outside bottom face 41e1 disposed on the circumference side of the cylindrical portion 41a and an inside bottom face 41e2 disposed at the approximate center of the outside bottom face 41e1. The inside bottom face 41e2 is formed in a disk shape having a predetermined radius. The outside bottom face 41e1 has a bottom face protruding to the outside (in the direction opposite to the opening) of the cylindrical portion 41a from the inside bottom face 41e2 and the lower surface has a hollow donut shape having a predetermined width. A height difference D is formed between the outside bottom face 41e1 and the inside bottom face 41e2 as shown in FIG. 7. A semi-spherical retaining portion 41e3 depressed toward the outside bottom face 41e1 from the inside bottom face 41e2 is formed at the center of the inside bottom face 41e2. The retaining portion 41e3 serves to hold the dome-shaped rear end portion constituting the body cover 11b of the capsule endoscope 2 and a cross-shaped projection portion 41e4 is formed toward the opening therein, which can allow sterilizing gas to invade the rear end portion of the body cover 11b retained in a line contact manner and to uniformly sterilize the entire rear end portion. The projection portion 41e4 may include a plurality of projections so as to hold the rear end portion in a point contact manner.

The handgrip portion 41b is formed of a plate member having an approximately triangular top surface and as shown in FIG. 5, the handgrip portion 42b of the inner cover portion 42 can abut thereon. The edge portion 41c has a predetermined width and is formed in a step shape higher by one step on the upper edge of the opening of the cylindrical portion 41a and the outer circumference of the handgrip portion 41b so as to suppress the movement of a handgrip portion of the inner cover portion 42 abutting on the handgrip portion 41b. The height of the edge portion 41c is equal to or greater than the thickness of the handgrip portion 42b or the edge portion 42c of the inner cover portion 42 abutting on the handgrip portion 41b and the sterilizing sheet 42 can be attached to the top surface of the edge portion 41c in the state where the inner cover portion 42 is accommodated in the blister pack 41.

The projection portion 41d includes approximately semi-cylindrical projections formed in the length direction of the cylindrical portion 41a, and the diameter of the upper end (on the opening side of the cylindrical portion 41a) is the largest and the diameter slowly decreases as it goes toward the lower end (toward the bottom face 41e side). The projections are disposed in the length direction of the cylindrical portion 41a with an approximately equal interval. In the projection portion 41d, the upper end is opened and the lower end forms a semi-dome shaped bottom. In this embodiment, five projections 41d are disposed on the circumferential surface of the cylindrical portion 41a with an approximately equal interval.

As shown in FIGS. 8 and 9, the inner cover portion 42 includes a cylindrical portion 42a having a bottom, a tongue-shaped handgrip portion 42b disposed in a part of the upper edge of the opening of the cylindrical portion 42a, the edge portion 42c extending from the handgrip portion 52b on the upper edge of the opening of the cylindrical portion 42a, and a plurality of semi-cylindrical projection portions 42d protruding externally from the inside of the cylindrical portion 42a.

As shown in FIGS. 8 to 12, the cylindrical portion 42a has a bottom face 42e and a hole portion 42e1 for retaining the capsule endoscope 2 is formed at the center of the bottom face 42e. The hole portion 42e1 has an approximately cylindrical convex section having a top surface protruding toward the inside of the cylindrical portion 42a (toward the opening) from the bottom face 42e and the inner diameter thereof is slightly greater than the outer diameter of the capsule endoscope 2. A plurality of straight-line shaped projections 42e2, that is, four projections in this embodiment, are formed in the length direction toward the opening of the hole portion 42e1. A step portion 42e3 is formed on the top surface side of the hole portion 42e1 and the inner diameter of the step portion 42e3 is smaller than the inner diameter of the opening side of the hole portion 42e1. As shown in FIG. 12, when the inner cover portion 42 is accommodated in the blister pack 41, the bottom face 42e including the hole portion 42e1 of the cylindrical portion 42a and the inside bottom face 41e2 including the retaining portion 41e3 of the blister pack 41 form a retention space area 40a according to the present invention and thus can receive and retain the capsule endoscope 2.

In this embodiment, as shown in FIGS. 9 and 12, when the front-head cover 11a of the capsule endoscope 2 is inserted into the hole portion 42e1, the projections 42e2 hold a part of the body cover 11b of the airtight container 11 in a line contact manner so that the mirror-finished portion 11a1 within the range of one-dot chained lines a and a is not in contact with the constituent parts of the hole portion 42e1 including the projections 42e2 and the step portion 42e3 and the end portion of the step portion 42e3 retains a part of the front-head cover 11a in a line contact manner. The projections 42e2 are not limited to the example where they are formed straightly in the length direction of the hole portion 42e1, but for example, a plurality of projections may be provided in the opening portion 42e1 so as to hold a part of the body cover 11b of the airtight container 11 in a point contact manner.

The handgrip portion 42b is formed of an approximately triangular plate member of which the top surface is smaller than the handgrip portion 41b and is formed integrally with the edge portion 42c formed on the upper edge of the opening of the cylindrical portion 42a, as shown in FIGS. 8 and 11. The handgrip portion 42b can abut on the handgrip portion 41b of the blister pack 41 when the inner cover portion 42 is accommodated in the blister pack 41. The edge portion 42c is formed on the upper edge of the opening of the cylindrical portion 42a and can abut on the upper edge of the opening of the blister pack 41 when the inner cover portion 42 is accommodated in the blister pack 41. As described above, the thickness of the handgrip portion 42b and the edge portion 42c is smaller than or equal to the thickness of the edge portion 41c of the blister pack 41. When the inner cover portion 42 is accommodated in the blister pack 41, the movement of the handgrip portion 42b is limited to the width of the handgrip portion 41b by the edge portion 41c. When the sterilizing sheet 43 is attached to the top surface of the edge portion 41c, the entire inner cover portion 42 including the handgrip portion 42b and the edge portion 42c is accommodated in the blister pack 41.

The projection portion 42d includes approximately semi-cylindrical projections extending in the length direction of the cylindrical portion 42a and the projections are disposed in the length direction of the cylindrical portion 42a with an approximately equal interval. The upper end of the projection portion 42d is opened and the lower end forms a semi-dome shaped bottom face. In this embodiment, five projection portions 42d are disposed on the circumferential surface of the cylindrical portion 42a with an approximately equal interval. In the projections 42d, in the state where the inner cover portion 42 is accommodated in the blister pack 41 and the handgrip portions 41b and 42b abut on each other, the most protruding portions of the projections 42d can come in contact with the inner circumferential surface of the cylindrical portion 41a, thereby preventing a loose play of the inner cover portion 42 in the blister pack 41.

As shown in FIGS. 5, 11, and 12, a passage 40b is formed between the inner circumferential surface of the projection portion 41d of the blister pack 41 and the outer circumferential surface of the cylindrical portion 42a of the inner cover portion 42 by a gap according to the present invention, thereby transmitting the sterilizing gas introduced from the outside through the sterilizing sheet 43. The passage 40b and the retention space area 40a communicate with each other, thereby allowing the sterilizing gas having passed through the passage 40b to reach the retention space area 40a.

Figure 2:
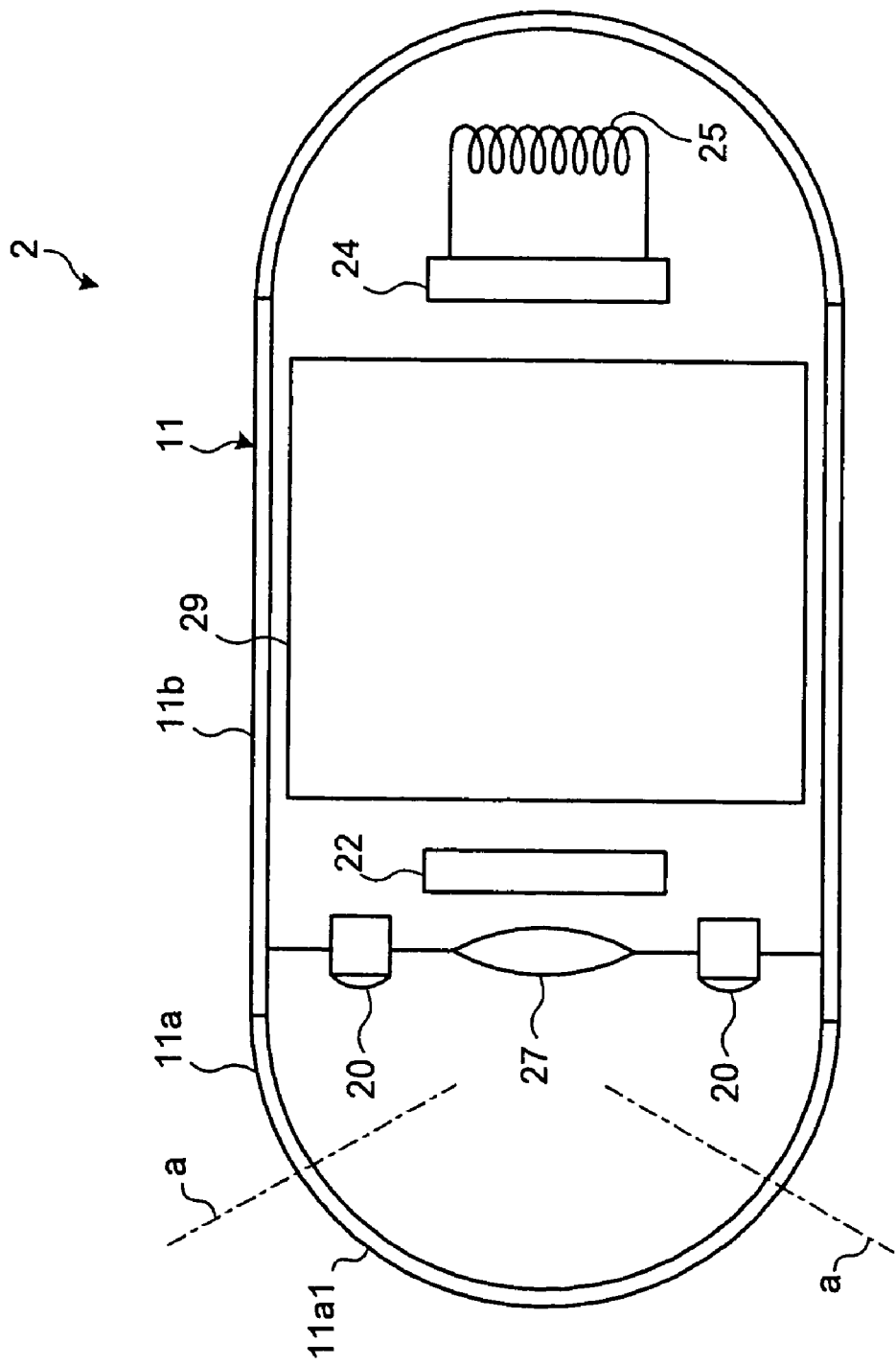
FIG. 2 is a side sectional view illustrating a schematic configuration of the capsule endoscope shown in FIG. 1.

The capsule endoscope 2 has a power-supply reed switch (not shown), which is turned on or off with an external magnetic field, therein and notifies to the outside that the reed switch is turned on and power is supplied to the respective function executing unit by means of lighting and extinguishing of the LED 20 shown in FIG. 2. Accordingly, at the time of use, the sterilizing sheet 43 is removed from the storage case 40, a magnetic body (magnet) is placed in the cylindrical portion 42a of the inner cover portion 42, and the reed switch is turned on by the magnetic field of the placed magnetic body, so that it is possible to confirm the lighting and extinguishing state of the LED 20 through the transparent or semi-transparent hole portion 42e1. That is, the hole portion 42e1 has a function of facilitating the confirmation of the lighting and extinguishing state of the LED, in addition to the function of retaining and protecting the capsule endoscope 2.

In this embodiment, when the inner cover portion 42 is accommodated in the blister pack 41, the manufactured capsule endoscope 2 is set into the storage case 40 by receiving the capsule endoscope 2 in the retention space area 40a formed by the bottom face 42e of the inner cover portion 42 and the inside bottom face 41e2 of the blister pack 41 and retaining the capsule endoscope with the retaining portion 41e3 and the hole portion 42e1. Next, by heat-sealing the sterilizing sheet 43 to the opening of the storage case 40 and then sterilizing the storage case 40 in an EOG manner as a whole, germs inside the storage case 40 are sterilized, thereby uniformly and satisfactorily sterilizing the entire capsule endoscope 2 retained in the retention space area 40a in a dot or line contact manner. In this embodiment, since new germs can be prevented from invading the storage case 40 by the heat-sealed sterilizing sheet 43, it is possible to maintain the sterilized state of the storage case.

Figure 13:
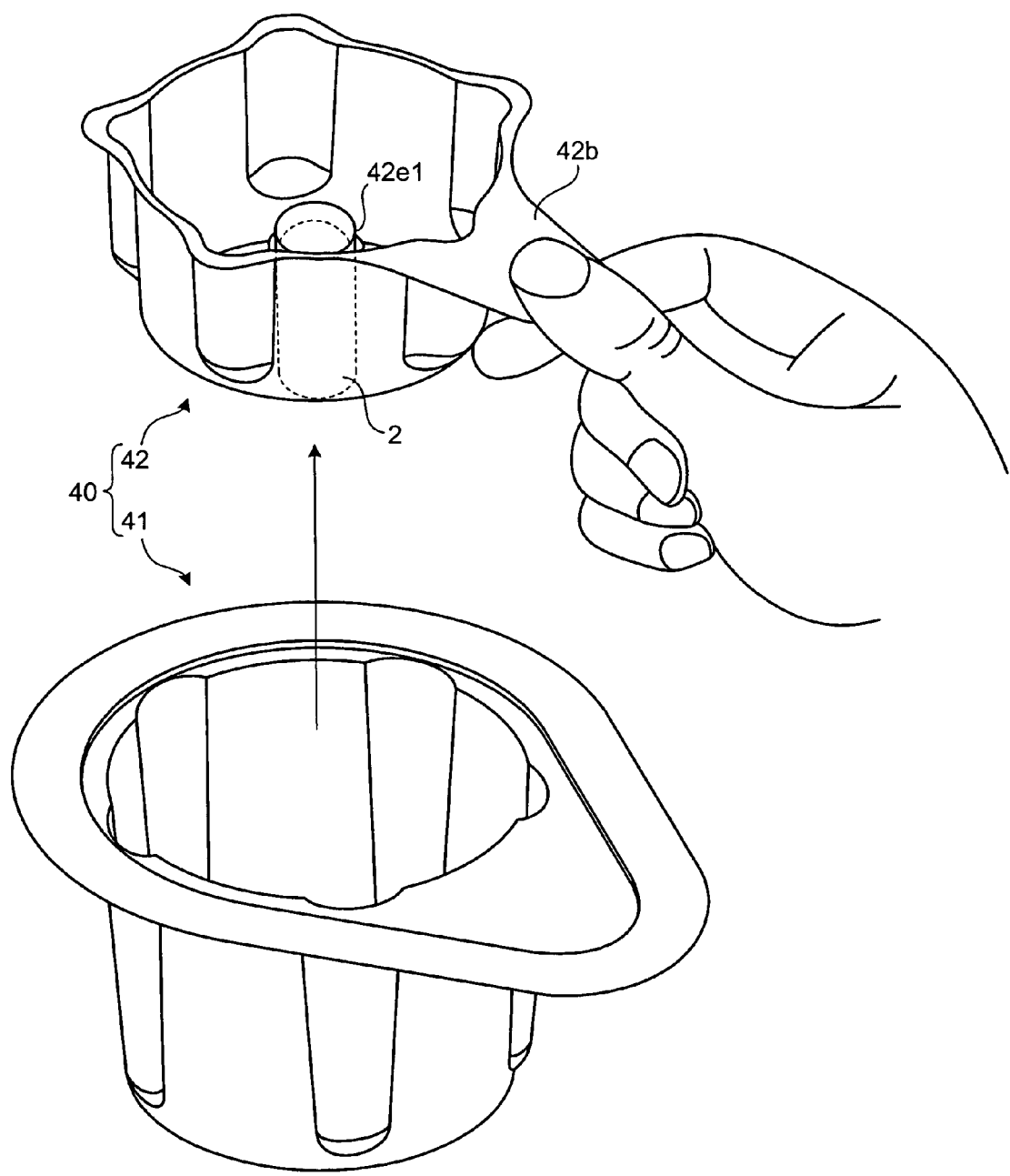
FIG. 13 is a perspective view illustrating a state where the inner cover portion is removed from the storage case shown in FIG. 5.

When it is used for a person to be examined, the sterilizing sheet 43 is removed from the storage case 40, the sterilized magnetic body is placed in the cylindrical portion 42a of the inner cover portion 42, and then the reed switch of the capsule endoscope 2 is turned on, thereby supplying power to the function executing unit from the battery 29. Next, as shown in FIG. 13, when the handgrip portion 42b of the inner cover portion 42 is grasped by fingers and the inner cover portion 42 is taken out of the blister pack 41, the capsule endoscope 2 can be taken out with the capsule endoscope retained in the hole portion 42e1 without contacting any hand. The inner cover portion 42 may be taken out by grasping the hole portion 42e1 from the inside of the inner cover portion 42 by fingers.

Accordingly, in this embodiment, since the passage and the retention space area communicating with the passage are formed between the blister pack and the inner cover portion, the capsule endoscope is accommodated in the retention space area, and the capsule endoscope is retained in a line contact manner, it is possible to safely retain the capsule endoscope. Since the opening of the blister pack is blocked with the sterilizing sheet having a sterilizing gas permeability so as to block the passage and the retention space area, the sterilizing gas can invade the contact portions of the capsule endoscope through the passage and the retention space area at the time of performing the gas sterilizing operation, thereby uniformly and satisfactorily sterilizing the entire capsule endoscope accommodated in the storage case.

Second Embodiment

Figure 14:
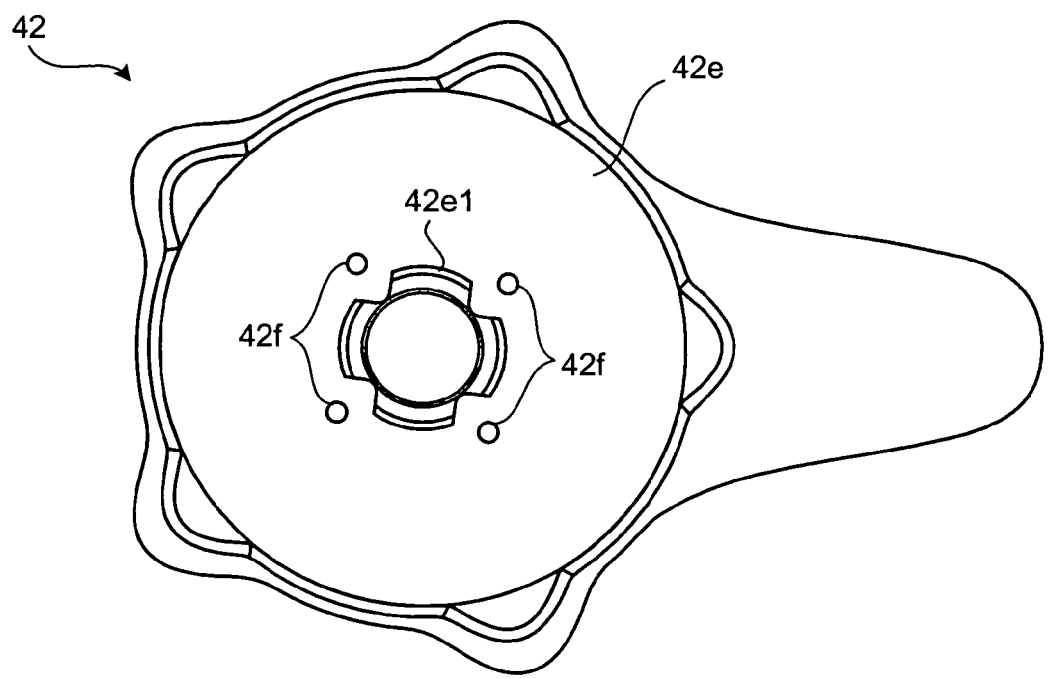
FIG. 14 is a top view illustrating an example of a top surface of a inner cover portion according to a second embodiment shown in FIG. 5.

FIG. 14 is a top view illustrating an example of a top surface of an inner cover portion according to a second embodiment shown in FIG. 5. In the following description with reference to the figures, the same elements as those of the first embodiment are denoted by the same reference numerals for the convenience. As shown in the figure, in the inner cover portion 42, a plurality of hole portions 42f, that is, four hole portions 42f in this embodiment, are formed in the bottom face 42e of the hole portion 42e1, thereby transmitting the sterilizing gas between the inside and the outside of the inner cover portion 42 through the hole portions 42f. By forming the hole portions 42f at positions close to the hole portion 42e1, the sterilizing gas can rapidly reach the capsule endoscope 2 retained in the hole portion 42e1, thereby more rapidly sterilizing the entire capsule endoscope 2 uniformly and satisfactorily.

Figure 15:
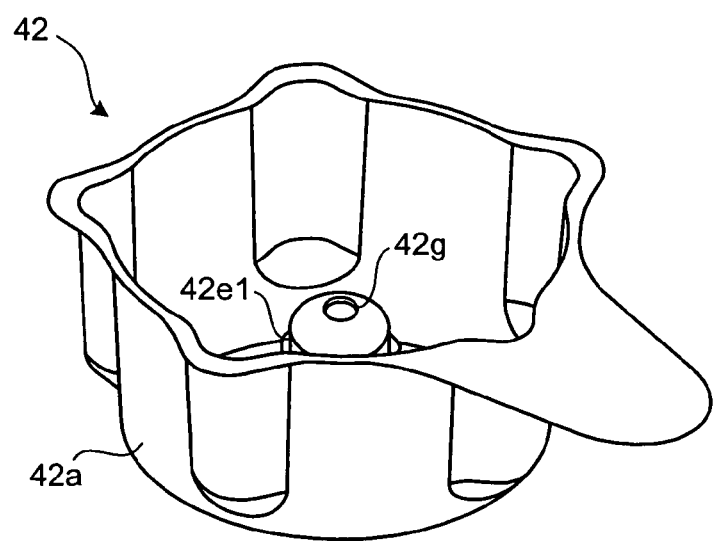
FIG. 15 is a perspective view illustrating another example of the configuration of the inner cover portion according to the second embodiment shown in FIG. 5.

FIG. 15 is a perspective view illustrating another example of the configuration of the inner cover portion according to the second embodiment shown in FIG. 5. As shown in the figure, in this embodiment, a hole portion 42g is formed at the vertex of the hole portion 42e1, thereby transmitting the sterilizing gas between the inside and the outside of the inner cover portion 42 through the hole portion 42g. Since the hole portion 42g is formed at the vertex of the hole portion 42e1 in which the capsule endoscope 2 is retained, the sterilizing gas can more rapidly reach the capsule endoscope 2, thereby more rapidly sterilizing the entire capsule endoscope 2 uniformly and satisfactorily.

The present invention is not limited to these two embodiments, but by combining the above-mentioned two embodiments, the hole portions 42f and 42g may be formed in the bottom face 42e and the vertex of the hole portion 42e1 or the hole portions may be formed in the peripheral surface of the hole portion 42e1. In these cases, it is possible to obtain the same advantages as the second embodiment. In addition, the hole portions may be formed in the peripheral surface of the cylindrical portion 42a of the inner cover portion 42.

Third Embodiment

Figure 16:
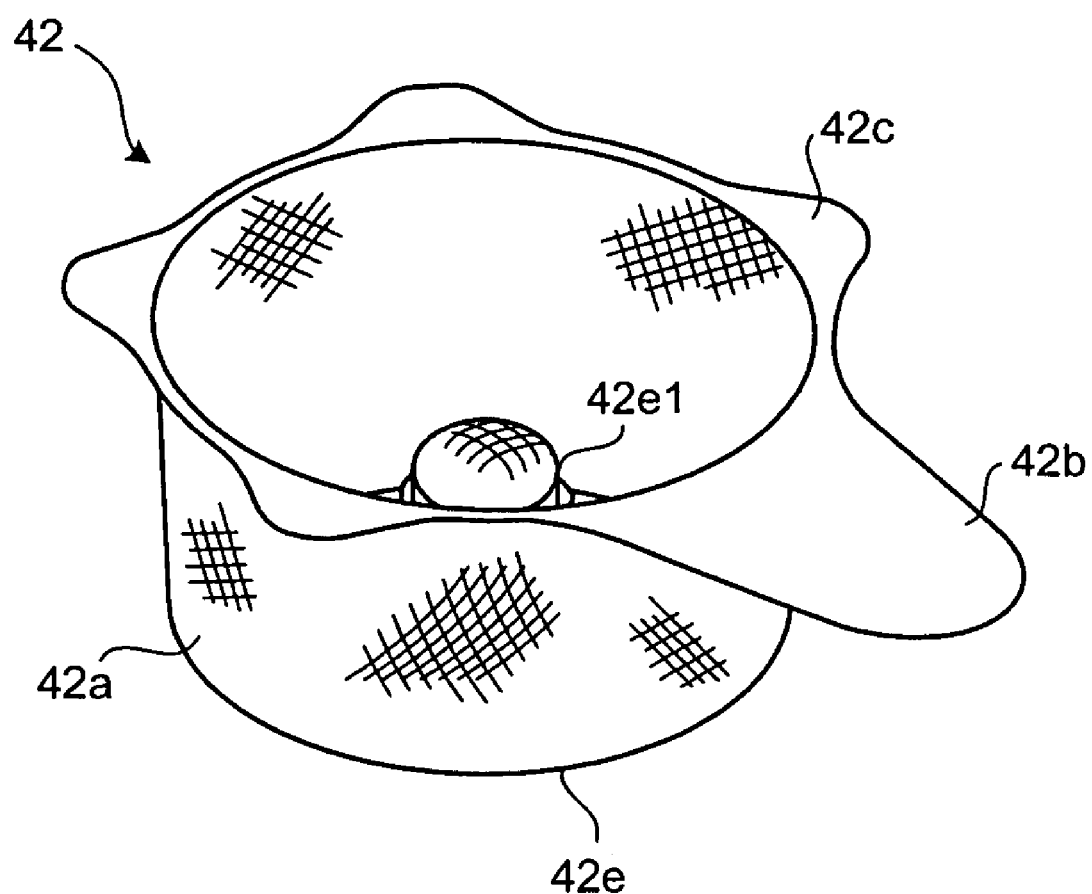
FIG. 16 is a perspective view illustrating a configuration of a inner cover portion according to a third embodiment shown in FIG. 5.

FIG. 16 is a perspective view illustrating a configuration of an inner cover portion according to a third embodiment shown in FIG. 5. As shown in the figure, in this embodiment, the parts other than the handgrip portion 42b and the edge portion 42c of the inner cover portion 42, that is, the cylindrical portion 42a, the bottom face 42e, and the hole portion 42e1, are formed in the form of meshes, thereby transmitting the sterilizing gas between the inside and the outside of the inner cover portion 42. In this embodiment, since the main parts of the inner cover portion 42 is formed in the form of meshes, the sterilizing gas can more rapidly reach the capsule endoscope 42, thereby more rapidly sterilizing the entire capsule endoscope 2 uniformly and satisfactorily.

The present invention is not limited to the embodiment, but only the peripheral surface, only the bottom face, or only the hole portion of the cylindrical portion 42a may be formed in the form of meshes or they may be combined.

INDUSTRIAL APPLICABILITY

As described above, the capsule endoscope storage case according to the present invention is useful for a medical observation device which is introduced into a human body to observe a portion to be examined and is suitable particularly for uniformly and satisfactorily sterilizing the entire capsule endoscope accommodated in the storage case.

The invention claimed is:

1. A capsule endoscope storage case, comprising:
a first retainer and a second retainer that form a retention space area for retaining a capsule endoscope therebetween, for accommodating and retaining the capsule endoscope in the retention space area; and
a sterilizing sheet that blocks the retention space area, the sterilizing sheet having a sterilizing gas permeability, wherein
the first retainer includes a cylindrical portion having a bottom, and the bottom face of the cylindrical portion includes an outside bottom face disposed on a circumference side of the cylindrical portion and an inside bottom face disposed at an approximate center of the outside bottom face,
the outside bottom face has a bottom face protruding in a direction opposite to an opening of the cylindrical portion from the inside bottom face, and
a semi-spherical retaining portion depressed toward the outside bottom face from the inside bottom face is formed at the center of the inside bottom face,
the second retainer includes a cylindrical portion having a bottom, and a hole portion, which has a top surface protruding toward the opening of the cylindrical portion from the bottom face of the cylindrical portion, is formed at the center of the bottom face of the cylindrical portion.

2. The capsule endoscope storage case according to claim 1, wherein one of the first and the second retainers is accommodated in the other one of the first and the second retainers.

3. The capsule endoscope storage case according to claim 1, further comprising a passage that enables passing of a sterilizing gas between the first and the second retainers.

4. The capsule endoscope storage case according to claim 1, further comprising a hole portion that enables passing of a sterilizing gas in at least one of the first and second retainers.

5. The capsule endoscope storage case according to claim 1, wherein at least one of the first and second retainers is formed in a mesh form which enables passing of a sterilizing gas.

6. The capsule endoscope storage case according to claim 1, wherein the first and the second retainers retain the capsule endoscope accommodated in the retention space area in one of a point contact manner and a line contact manner.

7. The capsule endoscope storage case according to claim 1, wherein the accommodated capsule endoscope is retained by at least one of the first and the second retainers, and accommodated in the retention space area.

8. The capsule endoscope storage case according to claim 1, wherein the retaining portion of the first retainer has a cross-shaped projection portion formed toward the opening of the cylindrical portion.

9. The capsule endoscope storage case according to claim 1, wherein the hole portion of the second retainer has an approximately cylindrical convex section, and a straight-line shaped projection is formed on an inner circumference of the hole portion in a length direction toward the opening of the hole portion.

10. The capsule endoscope storage case according to claim 1, further comprising a step portion that is formed on a top surface side of the hole portion, and having a smaller inner diameter than the inner diameter of an opening side of the hole portion.

* * * * *